April 18, 1972 E. S. BOERNER Plant Pat. 3,118
ROSE PLANT
Filed March 10, 1970
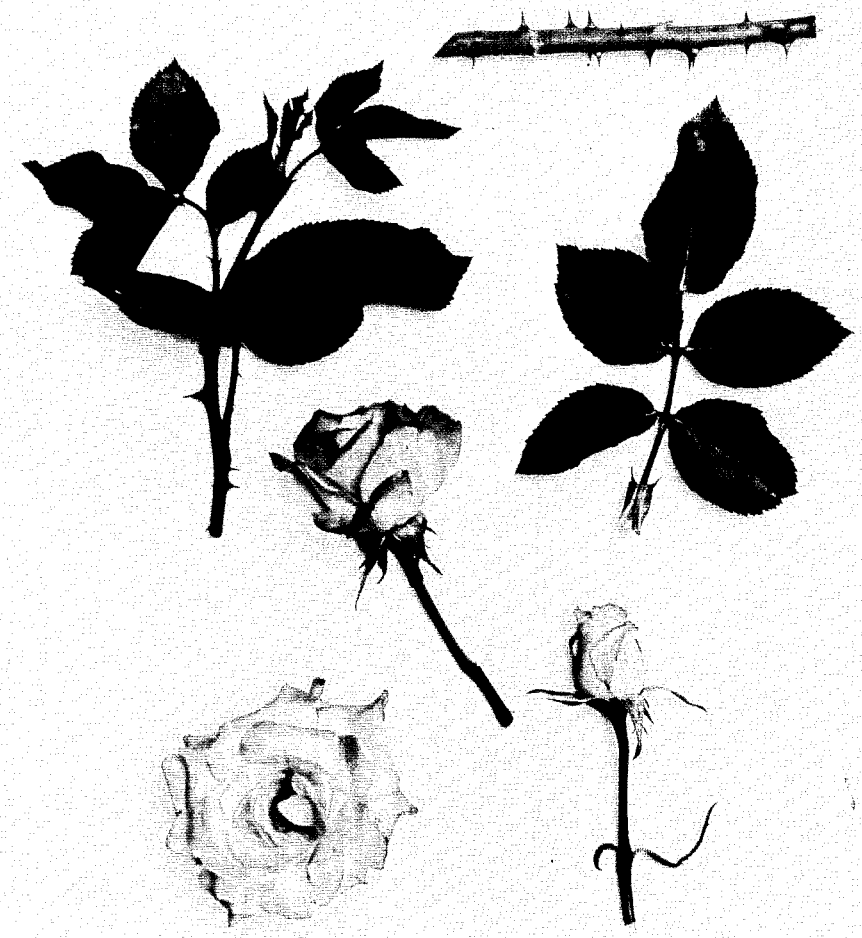
Inventor.
E. S. Boerner, Deceased
By: Lincoln Rochester Trust Company
By: Edward L. Jenner, Trust Officer
and Roger L. Boerner, Executors
By: Robb & Robb, Attorneys.

United States Patent Office

Plant Pat. 3,118
Patented Apr. 18, 1972

3,118
ROSE PLANT

Eugene S. Boerner, deceased, late of Benton, N.Y., by Lincoln Rochester Trust Co., Rochester, N.Y., and Roger L. Boerner, Milwaukee, Wis., executors, assignors to Jackson & Perkins Company, Newport Beach, Calif.

Filed Mar. 10, 1970, Ser. No. 18,356
Int. Cl. A01h *5/00*
U.S. Cl. Plt.—22 1 Claim

The present invention relates to a new and distinct variety of rose plant of the floribunda class, which was originated by the late Eugene S. Boerner, deceased, by crossing an unnamed and unpatented seedling of the rose variety known as "Lydia" (unpatented) with the rose variety known as "Starbright" (Plant Patent No. 2,128), the former being the seed parent and the latter being the pollen parent.

The primary objective of this breeding was to produce a new floribunda rose variety which bears multi-colored flowers on a bushy but compact plant. This objective was substantially achieved, along with other desirable improvements, as evidenced by the following unique combination of characteristics which are outstanding in the new variety and which distinguish it from its parents, as well as from all other rose varieties:

(1) A vigorous, well-branched and compact habit of growth of the floribunda type;
(2) A free-blooming habit throughout the season;
(3) Medium size flowers which are borne in small clusters and on lateral branches usually singly to a stem; and
(4) A distinctive, attractive and unusual flower color of Chinese Yellow which ages to Spinel Red on the outer edges of the petals at first, but later progressing to the center of the flower as the flower ages.

Asexual reproduction of the new variety by budding, as performed at Wasco, Calif., shows that the aforementioned characteristics and distinctions come true to form and are established and transmitted through succeeding propagations.

The accompaying drawing shows typical specimens of the vegetative growth and flowers of the new variety in different stages of development and as depicted in color as nearly true as it is reasonably possible to make the same in a color illustration of this character.

The following is a detailed description of the new variety, with the color terminology in accordance with Wilson's Horticultural Colour Chart, except where general color terms of ordinary dictionary significance are obvious:

Parentage: Seedling.
*Seed parent.*—An unnamed seedling of "Lydia."
*Pollen parent.*—"Starbright."
Classification:
*Botanic.*—Rosa hybrid.
*Commercial.*—Floribunda.
Propagation: Holds its distinguishing characteristics through succeeding propagations by budding.

*Flower*

(Observations made from specimens grown at Wasco, Calif. and Newport, Beach, Calif. in the afternoon during mid-October.)

Blooming habit: Recurrent—continuous.
Bud:
*Size.*—Small; from ¾ inch to 1 inch.
*Form.*—Urn-shaped.
*Color.*—When sepals first unfold—lower half of petals Chinese Yellow, Plate 606/1, lightened on upper half to Chinese Yellow, Plate 606/3, with areas longest exposed to sun darkening to between Spinel Red, Plate 0023 and Oxblood Red, Plate 00823/3. When half-blown—Inside of petals—outer edges between Spinel Red, Plate 0023 and Oxblood Red, Plate 00823/3, with area near flower center being Chinese Yellow, Plate 606/3. Reverse of petals—outer edges Spinel Red, Plate 0023, overlaying Chinese Yellow, Plate 606/3, with area near flower center ranging from Chinese Yellow, Plate 606/3 to Chinese Yellow, Plate 606/1 at base.
*Sepals.*—3 sepals lightly appendaged and 2 sepals having hairy edges. Color—inside—Spinach Green, Green, Plate 0960/3, with white tomentum. Outside—Spinach Green, Plate 0960/3.
*Receptacle.*—Shape—funnel. Size—small. Surface—smooth.
*Peduncle.*—Length—short. Surface—prickly. Strength—stiff; erect.
*Opening.*—Petals roll back individually; older outer petals become slightly pointed, and inner petals do not quill, but only roll back.
Bloom:
*Size.*—Medium. Average size when fully expanded—from 1¾ inches to 2 inches.
*Borne.*—Several together.
*Stems.*—Medium length; strong.
*Form (when first open).*—High-centered. Permanence—retains its form to the end.
*Petalage.*—Number of petals under normal conditions—approximately 25.
*Color.*—Center of flower—upper side of petals—outer area Spinel Red, Plate 0023, with areas shaded by other petals being near Chinese Yellow, Plate 606/1. Reverse side of petals—same as upper side.
*Outer petals*—similar to the others.
*Base of petals*—Chinese Yellow, Plate 606/1.
*General tonality from a distance*—multi-colored Spinel Red, Plate 0023 and Chinese Yellow, Plate 606/1. *Discoloration*—All colors deepen to Spinel Red, Plate 0023 over a period of 3 or 4 days.
*Fragrance.*—Slight. Nature—"Old Rose perfume."
Petals:
*Texture.*—Thick.
*Surface.*—Inside—satiny. Reverse—velvety.
*Shape.*—Round.
*Form.*—Tips slightly recurved.
*Arrangement.*—Imbricated.
*Petaloids in center.*—Few.
*Persistence.*—Hang on and dry.
*Lasting quality.*—On the plant—very long. As cut flower—very long.

*Reproductive organs*

Anthers: Medium size; regularly arranged around styles.
Filaments (threads): Medium length.
Pollen: Color—Lemon yellow.
Styles: Loosely separated; of uneven length.
Stigmas: Color—White.
Ovaries: All enclosed in calyx.

*Plant*

Form: Bush.
Growth: Vigorous; branching; compact.
Foliage:
*Leaves.*—Compound of 5 leaflets on normal mid-stem leaves.
Size—large. Quantity—normal. Color—new foliage—upper side—lighter than Spinach Green, Plate 0960/3. Reverse side—lighter than Spinach Green, Plate 0960/3, overlaid with Oxblood Red, Plate 00823/1.

*Leaflets.*—Shape—oval pointed. Texture — Upper side—leathery. Under side—velvety. Ribs and veins — ordinary. Edge — serrated. Serration — single; small. Petiole — under side prickly. Stipules—short; smooth.

*Disease resistance.*—Resistant to mildew and blackspot, as determined by comparison with other rose varieties grown under the same normal conditions at Wasco, Calif.

Wood:

*New wood.*—Color—Spinach Green, Plate 0960/3. Bark—smooth.

*Old wood.*—Color—Spinach Green, Plate 0960/1. Bark—smooth.

Thorns:

*Thorns.*—Quantity—On main stalks from base—ordinary. On laterials from stalk—ordinary. Form—Long; straight broad base. Color (when young)—Brown. Position—Irregular.

*Prickles.*—Quantity—On main stalks—few. On laterals—few. Color Brown.

*Short needles.*—Quantity—On main stalks—none. On laterals—none.

What is claimed is:

1. A new and distinct variety of rose plant of the floribunda class, substantially as herein shown and described, characterized particularly as to novelty by the unique combination of a vigorous, well-branched and compact habit of growth of the floribunda type, a free-blooming habit throughout the season, medium size flowers which are borne in small clusters and on lateral branches usually singly to a stem, and a distinctive, attractive and unusual flower color of Chinese Yellow which ages to Spinel Red on the outer edges of the petals at first, but later progressing to the center of the flower as the flower ages.

No references cited.

ROBERT E. BAGWILL, Primary Examiner